US009334358B2

(12) United States Patent
Rouse et al.

(10) Patent No.: US 9,334,358 B2
(45) Date of Patent: May 10, 2016

(54) OLIGOESTER

(75) Inventors: Sean Philip Nigel Rouse, Hull (GB); James Richard Humphrey, Hull (GB); Ben Cale, Selby (GB); David Freeman, Stockton-on-Tees (GB); Alun Barnes, Goole (GB)

(73) Assignee: CRODA INTERNATIONAL PLC, Goole, East Yorkshire (GB)

(*) Notice: Subject to any disclaimer, the term of this patent is extended or adjusted under 35 U.S.C. 154(b) by 0 days.

(21) Appl. No.: 13/810,087

(22) PCT Filed: Jul. 13, 2011

(86) PCT No.: PCT/GB2011/051316
§ 371 (c)(1),
(2), (4) Date: May 29, 2013

(87) PCT Pub. No.: WO2012/007754
PCT Pub. Date: Jan. 19, 2012

(65) Prior Publication Data
US 2013/0237672 A1    Sep. 12, 2013

(51) Int. Cl.
| | |
|---|---|
| C08G 63/12 | (2006.01) |
| C08L 67/00 | (2006.01) |
| A61K 8/36 | (2006.01) |
| A61K 8/37 | (2006.01) |
| A61Q 19/00 | (2006.01) |
| C08G 63/672 | (2006.01) |
| C08G 65/332 | (2006.01) |
| C08G 65/34 | (2006.01) |
| C11D 3/37 | (2006.01) |

(52) U.S. Cl.
CPC ............... *C08G 63/12* (2013.01); *A61K 8/361* (2013.01); *A61K 8/37* (2013.01); *A61Q 19/00* (2013.01); *C08G 63/672* (2013.01); *C08G 65/332* (2013.01); *C08G 65/3324* (2013.01); *C08G 65/34* (2013.01); *C08L 67/00* (2013.01); *C11D 3/3715* (2013.01); *A61K 2800/10* (2013.01); *C08G 2650/54* (2013.01)

(58) Field of Classification Search
CPC ..... A61K 8/361; A61K 8/37; A61K 2800/10; A61Q 19/00; C08G 63/12; C08G 63/672; C08G 65/34; C08G 65/332; C08G 65/3324; C08G 2650/54; C08L 67/00; C11D 3/3715

USPC .......................................... 525/437; 528/301
See application file for complete search history.

(56) References Cited

U.S. PATENT DOCUMENTS

| | | | | |
|---|---|---|---|---|
| 4,089,879 | A * | 5/1978 | Naskar et al. ................. | 554/164 |
| 6,242,499 | B1 | 6/2001 | Gruning et al. | |
| 7,407,667 | B2 | 8/2008 | Zerrer et al. | |
| 2005/0031580 | A1 * | 2/2005 | Allef et al. ................. | 424/78.37 |
| 2006/0166826 | A1 | 7/2006 | Zerrer et al. | |
| 2010/0256021 | A1 | 10/2010 | Muller et al. | |
| 2011/0201532 | A1 * | 8/2011 | Ponder et al. ................. | 510/220 |

FOREIGN PATENT DOCUMENTS

| | | |
|---|---|---|
| EP | 0051148 | 5/1982 |
| EP | 0499700 | 8/1992 |
| EP | 1683781 | 7/2006 |
| EP | 1857092 | 11/2007 |
| EP | 2036964 | 3/2009 |
| JP | H07-126603 | 5/1995 |
| JP | H10-114707 | 6/1998 |
| JP | 2008-239550 | 10/2008 |
| JP | 2009-126791 | 6/2009 |
| SU | 235658 | 1/1969 |
| WO | WO 2006/080390 | 8/2006 |
| WO | WO 2007/119047 | 10/2007 |

OTHER PUBLICATIONS

International Search Report dated Oct. 20, 2011 for PCT/GB2011/051316.
Official Action dated Jan. 27, 2015 from corresponding Russian Application No. 2013106260.
Official Action dated Feb. 3, 2015 from corresponding Japanese Application No. 2013-519158.

* cited by examiner

*Primary Examiner* — Randy Gulakowski
*Assistant Examiner* — Christopher M Rodd
(74) *Attorney, Agent, or Firm* — Jones Day

(57) ABSTRACT

Novel polyglycerol oligoesters derived from reaction of polyglycerol with a mixture of mono and diacids and also combinations of these novel polyglycerol oligoesters with known polyol monoesters, particularly known polyglycerol monoesters are disclosed. The use of these novel polyglycerol oligoesters and combination of esters as emulsifiers, solubilisers and/or thickeners especially in personal care formulations is also disclosed.

13 Claims, 2 Drawing Sheets

OLIGOESTER

CROSS REFERENCE TO RELATED APPLICATION

This application is the National Phase application of International Application No. PCT/GB2011/051316, filed Jul. 13, 2011, which designates the United States and was published in English. The foregoing related application, in its entirety, is incorporated herein by reference.

This invention relates to novel polyglycerol oligoesters derived from reaction of polyglycerol with a mixture of mono and diacids and also to combinations of the new polyglycerol oligoesters with known polyol monoesters, particularly known polyglycerol monoesters. The invention also relates to use of these esters and combination of esters as emulsifiers, solubilisers and/or thickeners especially in personal care formulations, health care formulations and home care formulations.

For effective emulsification and/or solubilisation in water based systems, for example oil in water emulsions, it is usually desirable to use emulsifiers and/or solubilisers which are relatively hydrophilic and are typically water soluble. Such surfactants usually have a high Hydrophile/Lipophile Balance (HLB), typically greater than 7 and commonly in the range 8 to 18. Conventionally such emulsification and solubilisation has been achieved by using ethylene oxide containing compounds, for example polyoxyethylene fatty ethers alone and in combination with polyoxypropylene fatty ethers, ethoxylated polyol monoesters, ethoxylated monoesters of fatty acids, ethoxylated esters of triglycerides, ethoxylated phosphate esters, ethoxylated fatty acids and ethoxylated glyceryl esters. A typical material used as a thickener is PEG-150 distearate. Pressure is being placed on the personal care industry to provide green products that are derived from renewable resources. Therefore there is pressure to move away from use of ethylene oxide which is typically derived from petrochemical feedstocks. Also 1,4 dioxane, which is reasonably anticipated to be a human carcinogen, may be formed as a by-product of reactions based on condensing ethylene oxide during the production of certain consumer products. Some environmental pressure groups are lobbying personal care businesses to remove this ingredient from products.

Non-ethylene oxide containing surfactants have been developed which are water soluble to replace these EO-containing materials. There are two key chemistry families namely ionic, typically anionic green surfactants where the water solubility is derived from the ionic charge on the material and non-ionic green surfactants where the water solubility is derived from the presence of ether, ester and/or hydroxyl functionalities.

For stable emulsions it is important that these surfactants are not too water soluble as they will then have a tendency to have a greater affinity for the water phase and will not remain at the oil/water interface long enough to achieve optimum emulsion stabilisation. The presence of the charge on ionic, namely anionic green surfactants has been found to render these materials too water soluble to achieve emulsion stability as good as their EO-containing counterparts. In some personal care applications the personal care formulations contain functional actives which are salts or actives which contain a significant quantity of salts as by-products. Anionic surfactants have been found to have poor electrolyte tolerance and hence a reduced emulsion stability.

Two examples of types of non-ionic green surfactants commercially available are sucrose monoesters and polyglycerol monoesters. Esterification of sucrose typically results in a mixture of mono, di and triesters. The presence of the di and tri esters reduces water solubility, HLB value and renders the material susceptible to electrolyte present in the emulsion. Therefore costly refining processes are required to remove the di and triesters making this an expensive emulsifier. Polyglycerol monoesters with typically more than 3 glycerol units tend to have HLB sufficiently high to be suitable as oil in water emulsifiers. However we have found that such products have poor electrolyte tolerance.

For solubilisation in personal care and home care formulations there are a variety of insoluble substances that may need to be solubilised, for example a range of essential oils, perfumes, fragrances, lipophilic actives, oily vitamins and emollient oils. It is important that the solubilisation produces as crystal clear a solution as possible as this solution is then added to a clear personal care or home care formulation. Therefore, it is key that the solubiliser itself is able to produce as crystal clear a solution as possible itself in water.

Ionic green surfactants available for solubilisation are similar chemistries to those available for emulsification. Ones that are currently commercially available as single solubilisers seem to have limited applications to a few fragrances and do not provide universal solubility across the wide variety of insoluble substances that are required to be solubilised.

Two examples of types of non-ionic green surfactants commercially available are sucrose monoesters and polyglycerol monoesters. The sucrose monoesters were analysed and found not to be water soluble enough to form a clear solution and the same was found to be the case for the majority of polyglycerol monoesters.

Blends of non-ionic and ionic green solubilisers are now being provided in the marketplace, for example blends of polyglycerol monoesters, anionic alkyl glucosides and alkyl glutamates. Again these appear to provide solubility across a limited range of insoluble substances, typically specific ranges of essential oils.

Thickeners tend to be incorporated into water based systems as levels of typically between 1 and 5% by weight and at such levels it is important that any designed EO-free thickeners provide adequate thickening properties whilst remaining clear in solution at such concentrations.

We have now surprisingly discovered a novel polyglycerol oligoester which by itself or in combination with known polyglycerol monoesters has emulsification and solubilising properties as good as the known ethylene oxide containing commercial products in defined emulsion systems and also overcomes some of the disadvantages, as discussed above, of current green ionic and non-ionic emulsifiers and solubilisers in defined systems. We have also found that this novel polyglycerol oligoester can provide good thickening properties whilst remaining clear in solution.

The invention accordingly provides a polyglycerol oligoester which is obtainable by reacting polyglycerol having from 3 to 20 glycerol units with a dicarboxylic acid or cyclic anhydride of such dicarboxylic acid having from 4 to 22 carbon atoms and a monocarboxylic acid having from 4 to 24 carbon atoms in a molar ratio from 1.5:1.0:0.1 to 3.0:1.0:3.0.

The polyglycerol of the polyglycerol oligoester has 3 to 20, preferably 4 to 10 glycerol units, especially 4 to 6 glycerol units. Manufacture of polyglycerol typically by polycondensation of glycerol leads to a mixture of oligomeric species both linear and cyclic, straight chained and branched. The products can then be refined to remove some unwanted species, for example polyglycerol for manufacture of polyglycerol monoesters for emulsification is refined to reduce the level of cyclic oligomers present. This is because it has been found that monoesters derived from cyclic polyglycerols have almost no emulsifying activity. Preferably the polyglycerol of the invention has an oligomer length distribution of 2 to 20 and more preferably 2 to 15.

Examples of suitable polyglycerols include polyglycerol-4, -6 and -10. A preferred polyglycerol of the current invention is polyglycerol-4.

The dicarboxylic acid is represented by the formula HOOC—R—COOH. R can be saturated or unsaturated, linear or branched and can be aromatic e.g. a phenyl ring (thus giving a phthalic, terephthalic or iso-phthalic dicarboxylic acid) or and desirably aliphatic, typically an alkylene or alkenylene group but also may be an alkoxy group as in diglycolic acid, and may be linear or branched, and may be cyclic though it is desirably open chain. Commonly R is a group $-(CH_2)_n-$, where n is from 2 to 20, usually from 2 to 14 and particularly from 2 to 8. Because mixtures of different dicarboxylic acids (or reactive derivatives) may be used to make materials used in practice, n may appear to be non integral, because it will be an average. The group R is usually unsubstituted, but may be substituted e.g. with hydroxyl and/or carboxyl groups as in malic acid (which has a hydroxyl) or citric acid (which has both). Preferred dicarboxylic acids include succinic, adipic, suberic, azelaic, sebacic and diglycolic. Especially preferred dicarboxylic acids are succinic and sebacic acids.

The monocarboxylic acid is represented by the formula $R^1COOH$ and $R^1$ is commonly a $C_3$ to $C_{23}$ aliphatic hydrocarbyl group. Desirably, $R^1$ is a $C_5$ to $C_{21}$, preferably $C_7$ to $C_{19}$, more preferably $C_7$ to $C_{13}$ alkyl, alkenyl or alkadienyl group. $R^1$ may be straight chain or branched and saturated or unsaturated. Examples of the monocarboxylic acid include valeric, caproic, enanthic, capric, caprylic, lauric, myristic, palmitic, stearic, iso-stearic, arachidic, behenic, oleic, linoleic, palmitoleic acid and mixtures thereof. Preferably the monocarboxylic acid is saturated. Preferably the monocarboxylic acid is straight chained. Preferred monocarboxylic acids include capric, caprylic, lauric, myristic and mixtures thereof with lauric acid being especially preferred.

Preferably the ratio of polyglycerol to dicarboxylic acid to monocarboxylic acid is 1.5:1.0:0.5 to 2.5:1.0:1.2. In an especially preferred use as an emulsifier the ratio of polyglycerol to dicarboxylic acid to monocarboxylic acid is 2.0:1.0:0.7. In an especially preferred use as a solubiliser the ratio of polyglycerol to dicarboxylic acid to monocarboxylic acid is 2.4:1.0:1.1.

The polyglycerol, dicarboxylic acid and monocarboxylic acid may be reacted together in a single stage reaction with or without the aid of a catalyst. Suitable examples of catalyst may include p-toluenesulfonic acid, methanesulfonic acid, organotitanates, organotin compounds; inorganic acids such as sulphuric, orthophosphoric and hypophosphorous acids, zeolites and bases such as potassium hydroxide, potassium carbonate and sodium hydroxide, biological agents such as enzymes and microorganisms. The reaction is typically carried out at a temperature ranging from 110 to 250° C., preferably 160 to 200° C. Alternatively the reactants may be reacted together in a two stage reaction where the polyglycerol and dicarboxylic acid are reacted together first with the aid of a catalyst (suitable examples are as disclosed for the one stage reaction) at a temperature ranging from 110 to 250° C. preferably 160 to 200° C. to form a precursor polyglycerol oligoester. The acid value of the reaction mixture is monitored and once it is in the range of 0 to 5 mgKOH/g then the monocarboxylic acid is added. It is not necessary to isolate and purify the precursor polyglycerol oligoester before addition of the monocarboxylic acid. In both cases the full reaction is carried out in a single pot either at atmospheric or sub ambient pressures. Preferably the reaction is carried out under a nitrogen atmosphere. Preferably any catalyst is removed or deactivated, for example by neutralisation, post reaction. A two stage reaction is preferred.

The invention accordingly includes a method of making of a polyglycerol oligoester as defined above by reacting polyglycerol having from 3 to 20 glycerol units with a dicarboxylic acid or cyclic anhydride of such dicarboxylic acid having from 4 to 22 carbon atoms and a monocarboxylic acid having from 4 to 24 carbon atoms in a molar ratio from 1.5:1.0:0.1 to 3.0:1.0:3.0 together in a single stage under esterification conditions.

The invention accordingly includes a method of making a polyglycerol oligoester as defined above by
a) reacting polyglycerol having from 3 to 20 glycerol units with a dicarboxylic acid or cyclic anhydride of such dicarboxylic acid having from 4 to 22 carbon atoms in a molar ratio from 1.5:1.0 to 3.0:1.0 under esterification conditions to form a precursor polyglycerol oligoester;
b) monitoring the esterification until the reaction mixture has reached an acid value of 0 to 5 mgKOH/g; then
c) adding 0.1 to 3.0 moles relative to dicarboxylic acid reactant of a monocarboxylic acid having from 4 to 24 carbon atoms.

Because of the number of carboxylic acid groups and hydroxyl groups available in the reaction mixture it is expected that a range of esterification products will be formed during either the one stage or two stage reaction processes. These may be crosslinked or non-crosslinked polymeric polyglycerol esters, linear and/or branched and/or cyclic, with full or partial esterification of the available hydroxyl groups.

The product polyglycerol oligoesters of the reaction are believed to comprise at least one, preferably linear, polyglycerol-dicarboxylic acid-polyglycerol polymeric sub unit as a major (greater than 50% by weight) constituent.

Preferably the precursor polyglycerol oligoester, as formed in the two stage reaction process, comprises a linear polyglycerol-dicarboxylic acid-polyglycerol as a major constituent.

The HLB for the polyglycerol oligoester is typically in the range from 7 to 18, preferably 10 to 18, more preferably 12 to 16. An especially preferred range for use as an emulsifier is 12 to 15. An especially preferred range for use as a solubiliser is 13 to 16.

Preferably the polyglycerol oligoester is non-ionic.

The polyglycerol oligoester of the invention is suitable to be used as an emulsifier, solubiliser and/or thickener preferably in personal care or home care formulations, specifically in oil in water emulsions.

Blends of polyglycerol oligoesters can also be used as emulsifiers and/or solubilisers.

Accordingly the present invention is also directed to a polyglycerol oliogoester as disclosed above which further comprises a second polyglycerol oligoester wherein the ratio of the first polyglycerol oligoester to the second polyglycerol oligoester ranges from 9:1 to 1:9, preferably 3:1 to 1:3 and more preferably 1.5:1 to 1:1.5.

Accordingly the present invention is also directed to the use of the polyglycerol oligoester described herein as an emulsifier, solubiliser and/or thickener in personal care and/or home care formulations.

Accordingly the present invention is also directed to a personal care and/or home care formulation comprising the polyglycerol oligoester described herein as an emulsifier, solubiliser and/or thickener.

The polyglycerol oligoesters are suitable for use as emulsifiers particularly in oil in water emulsions e.g. in personal care and/or home care applications. Personal care and/or home care emulsion products can take the form of creams, liquids and milks desirably and typically include emulsifier to aid formation and stability of the emulsion. Typically, personal care and/or home care emulsion products use emulsifiers (including emulsion stabilisers) in amounts of about 1 to about 20% by weight, most preferably 3 to 6% by weight of the emulsion.

The emulsifiers of the invention may also be combined with other emulsifiers and emulsion stabilisers in oil in water emulsions. Examples of such emulsifiers include non-ionic emulsifying waxes, for example fatty alcohols and polyol esters.

The oil in water emulsions comprising these emulsifiers may include various other personal care and/or home care ingredients. For example, suitable other ingredients include one or more ingredients such as cleansing agents, hair conditioning agents, skin conditioning agents, hair styling agents, antidandruff agents, hair growth promoters, perfumes, sunscreen compounds, pigments, moisturizers, film formers, humectants, alpha-hydroxy acids, hair colours, make-up agents, detergents, thickening agents, antiseptic agents, deodorant actives and surfactants, cleaning agents such as glass, window, bathroom, kitchen, hard surface cleaning agents, and the like, and degreasing agents.

The oil phase of such emulsions are typically emollient oils of the type used in personal care or cosmetic products or home care products, which are oily materials which are liquid at ambient temperature or solid at ambient temperature, in bulk usually being a waxy solid, provided they are liquid at an elevated temperature, typically up to 100° C. more usually about 80° C., so such solid emollients desirably have melting temperatures less than 100° C., and usually less than 70° C., at which it can be included in and emulsified in the composition.

The concentration of the oil phase may vary widely and the amount of oil is typically from 1 to 90%, usually 3 to 60%, more usually 5 to 40%, particularly 8 to 20%, and especially 10 to 15% by weight of the total emulsion. The amount of water present in the emulsion is typically greater than 5%, usually from 30 to 90%, more usually 50 to 90%, particularly 70 to 85%, and especially 75 to 80% by weight of the total composition. The amount of emulsifier used on such emulsions is typically from 0.1 to 10%, more usually 0.5 to 8%, more desirably 1 to 7%, particularly 1.5 to 6%, and especially 2 to 5.5%, by weight of the emulsion.

The end use formulations of such emulsions include in the field of personal care products: moisturizers, sunscreens, after sun products, body butters, gel creams, high perfume containing products, perfume creams, baby care products, hair conditioners, hair relaxer formulations, skin toning and skin whitening products, water-free products, anti-perspirant and deodorant products, tanning products, cleansers, 2-in-1 foaming emulsions, multiple emulsions, preservative free products, emulsifier free products, mild formulations, scrub formulations e.g. containing solid beads, silicone in water formulations, pigment containing products, sprayable emulsions, colour cosmetics, conditioners, shower products, foaming emulsions, make-up remover, eye make-up remover, and wipes.

The end use formulations of such emulsions include in the field of home care products: home cleaning products and detergents, both industrial and domestic, window cleaning products, glass cleaning products, bath and/or shower cleaning products, kitchen cleaning products, surface cleaning products, degreasing products, air fresheners, hard surface modification products, fabric cleaning products such as washing liquids and fabric conditioners, carpet cleaning products, hard floor cleaning products, anti-bacterial products, sprays and wipes, sterilisation products, and the like.

Such formulations include green formulations, natural formulations and naturally certified formulations.

A further use of such emulsifiers is to reduce irritation of primary surfactants such as alkyl ether sulphates and alkyl sulphates, for example in baby care formulations or cleaning products for items used by infants. End use formulations of such emulsions include mild and/or sulphate free detergents, microemulsions, cleansers including acne cleansers, shampoos, including 2in1 with conditioners, and baby shampoos, facial and body washes, shower gels and shower creams, hand soaps including cream hand soaps.

The polyglycerol oligoesters are also suitable for use as emulsifiers in oil in water emulsions in health care applications. Examples include liquid emulsion oral treatments, medical shampoos, topical treatment creams, lotions and ointments, anti-acne treatment creams, lotions and tonics, suppositories.

The polyglycerol oligoesters are suitable for use as solubilisers, particularly in personal care and/or home care formulations. The solubilisers are key components of aqueous based systems that incorporate oily components such as perfumes, essential oils, lipophilic actives, oily vitamins and emollient oils. Presolubilisation of these oily components into the personal care and home care formulations ensures an acceptable clear product. Typical products that can benefit from the use of the solubilisers include clear shampoos, sulphate free shampoos, clear combined shampoos and conditioners, clear conditioners, clear facial washes, clear shower gels and bath foams, clear hair and skin gels, aqueous/alcoholic hair spritzes, aqueous/alcoholic body sprays, aftershaves, colognes, skin cleansers and toners, make up removers, anti-bacterial wipes, lotions, ointments and gels, general wet wipes, home cleaning products and detergents, both industrial and domestic, window cleaning products, glass cleaning products, bath and/or shower cleaning products, kitchen cleaning products, surface cleaning products, degreasing products, and the like. Such formulations include green formulations, natural formulations and naturally certified formulations.

Typically the solubiliser is used in an aqueous based system in a solubiliser to oil ratio of 0.5:1 to 50:1, more preferably 1:1 to 20:1 and especially 1:1 to 10:1.

A further use of such solubilisers is to reduce irritation of primary surfactants such as alkyl ether sulphates and alkyl sulphates, for example in baby care formulations.

The polyglycerol oligoesters are also suitable for use as solubilisers in oil in water emulsions in health care applications. Examples include liquid emulsion oral treatments, medical shampoos, topical treatment creams, lotions, ointments and cleansing wipes, anti-acne treatment creams, lotions and tonics.

The polyglycerol oliogesters of the invention are also suitable for use as thickening agents in detergent systems. Applications include mild detergents, sulphate free detergents, microemulsions, cleansers including acne cleansers, shampoos in general, baby shampoos and 2 in 1 shampoos and conditioners, facial and body washes, shower creams and gels, hand soaps. Typically the thickening agent is present at levels of 1 to 5% by weight in the detergent system. As for use as solubilisers it is key that the polyglycerol oligoesters remain clear in solution at the relevant concentration levels.

The ability of the polyglycerol oligoester to function as an emulsifier, solubiliser and/or thickener can be further enhanced by the addition of a polyol monoester. Most preferably the ability of the polyglycerol oligoester to function as a solubiliser is further enhanced by the addition of a polyol monoester.

Accordingly the present invention is also directed to a blend of:
  a) a polyglycerol oligoester which is obtainable by reacting polyglycerol having from 3 to 20 glycerol units with a dicarboxylic acid or cyclic anhydride of such dicarboxylic acid having from 4 to 22 carbon atoms and a monocarboxylic acid having from 4 to 24 carbon atoms in a molar ratio from 1.5:1.0:0.1 to 3.0:1.0:3.0; and
  b) a polyol monoester,
wherein the ratio of a):b) ranges from 5.0:1.0 to 1.0:5.

Furthermore the present invention includes use of the blend defined above as an emulsifier, solubiliser and/or thickener, preferably as a solubiliser in personal care, health care and/or home care formulations.

Accordingly the present invention is also directed to a personal care, health care and/or home care formulation comprising the blend defined above as an emulsifier, solubiliser and/or thickener, preferably as a solubiliser.

The polyol monoester is typically derived from the esterification of a polyol with a monocarboxylic acid. Examples of suitable polyols include neopentyl polyols, sugar derived polyols, glycerol and polyglycerols. Neopentyl polyols include pentaerthyritol, polypentaerythritols such as di- and tripentaerthyritol, trimethylol alkanes such as trimethylol propane, and neopentyl glycol. Sugar derived polyols include $C_4$ polyols such as threitol and erythritol, $C_5$ polyols such as inositol, arabitol and xylitol and $C_6$ polyols such as sorbitol. Preferably the polyol is chosen from neopentyl polyols and polyglycerols, more preferably polypentaerythritols and polyglycerols and especially polyglycerol.

The polyglycerol of the polyglycerol monoester has 3 to 20, preferably 4 to 10 glycerol units, especially 4 to 6 glycerol units. Manufacture of polyglycerol typically by polycondensation of glycerol leads to a mixture of oligomeric species both linear and cyclic, straight chained and branched. The products can then be refined to remove some unwanted species.

Examples of suitable polyglycerols include polyglycerol-4, -6 and -10. An especially preferred polyglycerol for manufacture of the polyglycerol monoester of the current invention is polyglycerol-6.

The monocarboxylic acid for manufacture of the polyol monoester is represented by the formula $R^2COOH$ and $R^2$ is commonly a $C_3$ to $C_{23}$ aliphatic hydrocarbyl group. Desirably, R2 is a $C_5$ to $C_{21}$, preferably $C_7$ to $C_{19}$, more preferably a $C_7$ to $C_{13}$ alkyl, alkenyl or alkadienyl group. $R_2$ may be straight chain or branched and saturated or unsaturated. Examples of the monocarboxylic acid include valeric, caproic, enanthic, capric, caprylic, lauric, myristic, palmitic, stearic, iso-stearic, arachidic, behenic, oleic, linoleic, palmitoleic acid and mixtures thereof. Preferably the monocarboxylic acid is saturated. Preferably the monocarboxylic acid is straight chained. Preferred monocarboxylic acids include capric, caprylic, lauric, myristic and mixtures thereof.

Preferably the ratio of a):b) is 3.0:1.0 to 1.0:3.0 and even more preferably the ratio of a):b) is 1.5:1.0 to 1.0:1.5.

The novel polyglycerol oligoester of the present invention can be used as a solubiliser for solubilising fragrance oils which are otherwise very difficult to solubilise. According to a further aspect of the invention, therefore, there is provided an EO free solubiliser having a very high efficiency for the solubilisation of fragrances and other lipophilic substances comprising a combination of
  a) the polyglyceryl oligoester of the present invention;
  b) a polyglyceryl monoester, and
  c) a polyol co-surfactant and/or a lipophilic co-solvent.

Preferably the solubiliser comprises the following;
1) A novel polyglyceryl oligoester as previously described, more preferably polyglycerol oligoester where the monoacid has a linear alkyl chain of $C_{7\text{-}C14}$, and which has a high solubility in water.
2) A polyglycerol mono ester, where the polyglycerol oligomer has a chain length of $C_{2\text{-}20}$, more preferably $C_{4\text{-}10}$. The alkyl chain of the monoester preferably comprises a residue of a $C_{6\text{-}22}$ linear fatty acid, more preferably with an alkyl chain length of $C_{8\text{-}14}$.
3) A polyol co-solvent. This could be any polyol, preferably a polyol with a molecular weight of 200 Da or less, more preferably glycerine, 1,3 propane diol, propylene glycol, sorbitol or butylene glycol.
4) A co-solvent. This is preferably a lipophilic substance for which the solubiliser system (comprising the first two or three components) has a very high affinity. The co-solvent is preferably a 'green' (eg. non-alkoxylated), liquid, cosmetic oils. Preferably, the co-solvent is a liquid fatty acid, liquid fatty alcohol, fatty acid ester of isopropanol, ester of liquid fatty alcohols and liquid fatty acids which result in a liquid esterified oil, glyceryl ester of liquid fatty acids and/or naturally derived apolar oil. More preferably, the co-solvent is a fatty acid, preferably capric acid, caprylic acid, oleic acid, isostearic acid, oleyl alcohol, isostearyl alcohol, isopropyl isostearate, isostearyl isostearate, glyceryl isostearate and/or squalane (olive oil derived).

Components 1, 2, 3 & 4 as described above may be present in the solubiliser in combinations as follows: 1+2, 1+2+3, 1+2+4, or 1+2+3+4.

Preferably, the ratios of the components present in these combinations are in the range of: Combination 1+2: 0.1:0.9 to 0.9:0.1, more preferably 0.3:0.7 to 0.7:0.3.
Combination 1+2+3: 1+2 in the ratios above, and (1+2):3 at 0.6:0.4 to 0.95:0.05, more preferably 0.7:0.3 to 0.9:0.1.
Combination 1+2+4: 1+2 in the ratios above, and (1+2):4 at 0.6:0.4 to 0.95:0.05, more preferably 0.7:0.3 to 0.9:0.1.
Combination 1+2+3+4: 1+2 in the ratios above, and ratios of (1+2):(3+4) at 0.6:0.4 to 0.95:0.05, more preferably 0.7:0.3 to 0.9:0.1. The ratio 3:4 in the part (3+4) is preferably 0.9:0.1 to 0.1:0.9, more preferably 0.7:0.3 to 0.3:0.7.

Alternatively, the ability of the polyglycerol oligoester to function as an emulsifier and/or thickener can be further enhanced by the addition of an interfacially active wax. Preferably, the combination of the novel polyglycerol oligoester and an interfacially active wax provides an emulsifying wax. Preferably, the emulsifying wax can be substituted for any traditional emulsifying wax in personal care, health care and/or home care applications.

It has been discovered that it is possible to produce an emulsifying wax using the novel oligoester previously described and an interfacially active wax. Preferably, the emulsifying wax comprises a polyglyceryl oligoester which is polyglycerol-2 to polyglycerol-10:$C_{2\text{-}10}$ di-acid:$C_{7\text{-}36}$ mono acid, more preferably polyglycerol-4 to polyglycerol-10:$C_{2\text{-}6}$ di-acid:$C_{12\text{-}22}$ mono acid, or more preferably still polyglycerol-4 to polyglycerol-10:$C_4$ di-acid:$C_{16\text{-}22}$ mono acid. The oligoester preferably has a polyglycerol:di-acid:monoacid ratio in the range of 1.5:1.0:0.1 to 3.0:1.0:3.0.

The interfacially active wax is preferably a glyceryl ester of a fatty acid. Examples of suitable glyceryl esters of fatty acids include, but are not limited to, sorbitan esters of fatty acids, fatty acids, fatty alcohols, ethoxylated fatty acids or alcohols where the ethoxylation level is 5 moles or less. More preferably, the wax is a glyceryl ester of a fatty alcohol or fatty acid with an alkyl chain length of $C_{14-36}$, or more preferably still $C_{16-22}$. Glyceryl esters of fatty acids, preferably those with fatty acid chain lengths of $C_{14-36}$, or more preferably still $C_{16-22}$, with a mono-alkyl content of between 40-90%. Any variant of novel polyglyceryl oligoester as described above can be used with any interfacially active wax to give the desired viscosity increase and emulsion droplet size reduction properties to give a stable cream. The ratio of the novel oligoester to the interfacially active wax is preferably between 0.6 to 0.4 and 0.1 to 0.9 for the polyglyceryl oligoester:wax, more preferably between 0.5:0.5 and 0.25:0.75.

It is preferable to use more than one interfacially active wax from the list above to produce the emulsifying wax. In this case, for example, the polyglyceryl oligoester:total wax ratio is preferably between 0.6 to 0.4 and 0.1 to 0.9, more preferably between 0.5:0.5 and 0.25:0.75, where the total wax can be a combination of any of the interfacially active waxes described above. Where two of the said waxes are present in the emulsifying wax, they are preferably present at a ratio of between 0.1:0.9 and 0.9:0.1. More preferably, wax combinations comprise linear fatty $C_{16-22}$ alcohols and glyceryl esters of linear fatty acids with chain lengths of $C_{16-22}$, with a mono-alkyl content of 40-90%.

Any of the above features may be taken in any combination, and with any aspect of the invention.

EXAMPLES

Figure 1:
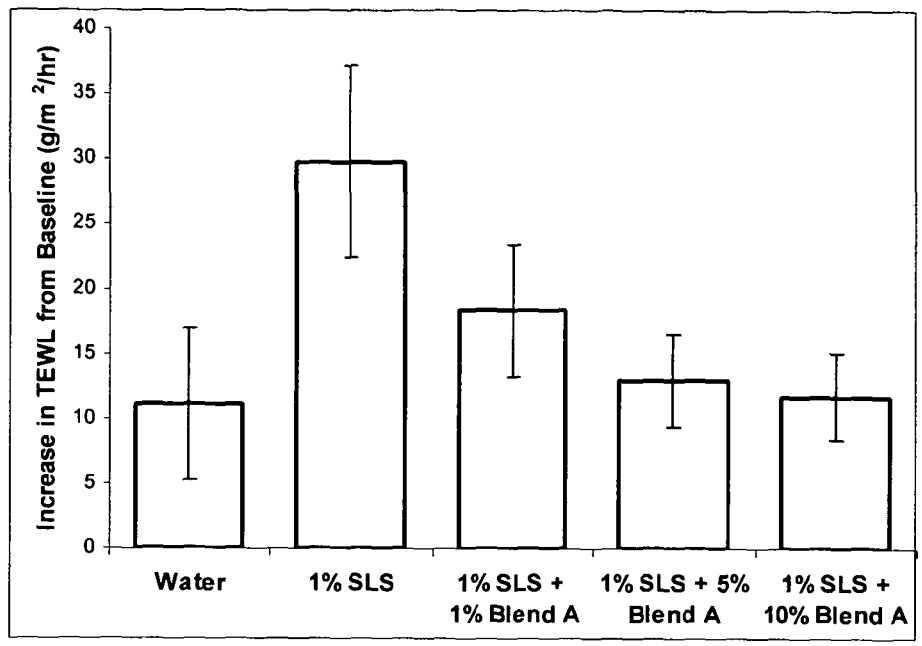
FIG. 1: Is a graph reporting Basal TEWL results of Blend A with sodium lauryl sulphate (SLS).

The invention is illustrated by the following non-limiting examples. All parts and percentages are by weight unless otherwise stated.

Example 1

A: 2-Stage Preparation of Novel Polyglycerol Oligoester (Examples E1-11 & S1-3)

Succinic acid (52.67 g, 0.4460 moles), polyglycerol-4 ex Solvay (280.39 g, 0.8920 moles) and 50% aqueous hypophosphorous acid catalyst (2.00 g, 0.0152 moles) were heated with stirring under nitrogen to 200° C.

The reaction mixture was held at 200° C. for 4 hours and then monitored until the acid value was less than 5 mgKOH/g. Lauric acid was then added (66.94 g, 0.3345 moles). The reaction mixture was held at 200° C. for a further 4 hours and then monitored until the acid value was less than 3 mgKOH/g. Potassium hydroxide was then added (1.0 g 85%, 0.0152 moles) to neutralise the catalyst. The reaction mixture was monitored until and the acid value was below 1 mgKOH/g. The product was then cooled to 80° C. and discharged.

Further examples of novel polyglycerol oligoester were made by the above method with differing starting materials, proportions and reaction temperatures. Neutralisation was not always carried out. Details are shown in Table One. In the Table, E means it was tested for use as an emulsifier, and S for use as a solubiliser as disclosed in Examples below.

Note that such labelling of the polyglycerol oligoester as E does not mean it cannot be used as a solubiliser and/or thickener. It just means that is what Examples have been provided for.

B: One-Stage Preparation of Novel Polyglycerol Oligoester (Examples E12-17)

Succinic acid (30.36 g, 0.2571 moles), polyglycerol-6 ex Spiga Nord (237.80 g, 0.5142 moles), palmitic acid (131.84 g, 0.5142 moles) and catalyst 85% potassium hydroxide pellets (1.00 g, 0.0152 moles) were heated with stirring under nitrogen to 250° C.

The reaction mixture was held at 250° C. for 4 hours and then monitored until the acid value was less than 1 mgKOH/g. The product was then cooled to 80° C. and discharged.

Further examples of novel polyglycerol oligoester were made by the above method with differing starting materials, proportions and reaction temperatures. Details are shown in Table One.

Note that such labelling of the polyglycerol oligoester as E does not mean it cannot be used as a solubiliser and/or thickener. It just means that is what Examples have been provided for.

C: Preparation of Polyol Monoester for Blending with Novel Polyglycerol Oligoester Capric/Caprylic acid (100.68 g, 0.6472 moles), polyglycerol-6 (299.32, 0.6472 moles) and 50% aqueous hypophosphorous acid catalyst (2.00 g, 0.0152 moles) were heated with stirring under nitrogen to 200° C. The reaction mixture was held at 200° C. and the acid value monitored until it was below 1 mgKOH/g. The product was then cooled to approximately 80° C. and discharged.

A further polyglycerol monoester was made by the general method set out in C but making changes to the starting materials, material proportions or reaction conditions. Details are shown in Table One. The abbreviation PME illustrates polyol monoester.

Materials in Table One
Polyglycerols
PG4SN polyglycerol-4 ex-Spiga Nord Spa (oligomer length 4 to 13)
PG4SOL polyglycerol-4 ex-Solvay (oligomer length 3 to 10)
PG6 polyglycerol-6 ex-Spiga Nord Spa
PG10 polyglycerol-10 ex-Lonza
  Diacids
DAC4 succinic acid
DAC2OC2 diglycolic acid
DAC6 adipic acid
DAC8 suberic acid
DAC9 azelaic acid
DAC10 sebacic acid
  Mono-Acids
MAC8/10 capric/caprylic acid
MAC12 lauric acid
MAC16 palmitic acid
MAC18 stearic acid
  Catalysts
Cat 1 $H_3PO_2$
Cat 2 KOH
  Catalyst Neutralisation Agents
Neut 1 85% KOH pellets
Neut 2 0.85M aqueous KOH

TABLE ONE

| Ex. No | Polyglycerol Type | mol | Diacid type | mol | Monoacid Type | mol | Catalyst Type | % w/w | Reaction temp | Neutral. agent |
|---|---|---|---|---|---|---|---|---|---|---|
| E1  | PG4SOL | 2 | DAC4    | 1 | MAC12   | 0.75 | Cat 1 | 0.25 | 200 | Neut 1   |
| E2  | PG4SN  | 2 | DAC6    | 1 | MAC12   | 1    | Cat 1 | 0.3  | 180 | Not used |
| E3  | PG4SN  | 2 | DAC2OC2 | 1 | MAC12   | 1    | Cat 1 | 0.3  | 180 | Not used |
| S1  | PG4SN  | 2 | DAC10   | 1 | MAC12   | 1    | Cat 1 | 0.3  | 180 | Not used |
| S2  | PG4SN  | 2 | DAC8    | 1 | MAC12   | 1    | Cat 1 | 0.3  | 180 | Not used |
| S3  | PG4SN  | 2 | DAC9    | 1 | MAC12   | 1    | Cat 1 | 0.3  | 180 | Not used |
| E4  | PG6    | 2 | DAC4    | 1 | MAC12   | 1    | Cat 1 | 0.3  | 180 | Not used |
| E5  | PG10   | 2 | DAC8    | 1 | MAC12   | 1    | Cat 1 | 0.3  | 180 | Not used |
| E6  | PG10   | 2 | DAC4    | 1 | MAC12   | 1    | Cat 1 | 0.3  | 180 | Not used |
| E7  | PG4SN  | 2 | DAC4    | 1 | MAC12   | 0.75 | Cat 1 | 0.25 | 180 | Neut 2   |
| E8  | PG4SN  | 2 | DAC4    | 1 | MAC8/10 | 1    | Cat 1 | 0.3  | 180 | Not used |
| E9  | PG4SN  | 2 | DAC4    | 1 | MAC12   | 0.5  | Cat 1 | 0.3  | 180 | Not used |
| E10 | PG6    | 2 | DAC4    | 1 | MAC16   | 2.0  | Cat 2 | 0.25 | 250 | Not used |
| E11 | PG6    | 2 | DAC4    | 1 | MAC16   | 0.9  | Cat 2 | 0.25 | 250 | Not used |
| E12 | PG6    | 2 | DAC4    | 1 | MAC16   | 0.75 | Cat 2 | 0.25 | 250 | Not used |
| E13 | PG4SN  | 2 | DAC4    | 1 | MAC16   | 0.75 | Cat 2 | 0.25 | 230 | Not used |
| E14 | PG10   | 2 | DAC4    | 1 | MAC18   | 0.75 | Cat 2 | 0.25 | 250 | Not used |
| E15 | PG10   | 2 | DAC4    | 1 | MAC16   | 0.75 | Cat 1 | 0.25 | 250 | Not used |
| PME 1 | PG6   | 1 |         |   | MAC8/10 | 1    | Cat 1 | 0.25 | 180 | Not used |
| PME 2 | PG4SN | 1 |         |   | MAC8/10 | 1    | Cat 1 | 0.25 | 200 | Not used |

Example 2

Each E product of Table One was tested for its emulsification properties in a variety of oils using the following test. In a 50 g vessel oil (20% by weight), Xanthan gum (2% aqueous solution, 5.0% by weight), deionised water (73.0% by weight) and emulsifier (2.0% by weight) were added. Each formulation was heated to 80° C. held for 20 mins and then homogenised for 10,000 rpm before being left to cool to room temperature. The formulated emulsions were split into four 10 g portions and in two cases 0.5 g NaCl was added. The samples were then checked for stability over a defined time period at room temperature.

Table Two contains the results.
Materials in Table Two
Oils
GTCC Crodamol GTCC ex Croda
IPM Crodamol IPM ex Croda
  Comparative Emulsifiers
Crillet 3 EO-containing ex Croda
Brij S20EO-containing ex Croda
Polyaldo 10-1-O KFG polyglycerol monoester ex Lonza (green emulsifier)
Natpure SOL comprises natural sucrose and vegetable derived fatty acid monoesters (green emulsifier/solubiliser)

TABLE TWO

| | Oil | | | | | | | | |
|---|---|---|---|---|---|---|---|---|---|
| | GTCC | | | GTCC (5% NaCl) | | | IPM | | |
| Emulsifier | day | week | month | day | week | month | day | week | month |
| E1 | C | C | C | C | C | C | C | C | C |
| E2 | C | C | C | C | C | C | C | C | C |
| E3 | C | C | C | C | C | C | C | C | C |
| E4 | C | C | C | C | C | C | C | C | C |
| E5 | C | C | C | CS | CS | CS | C | C | CC |
| E6 | C | C | C | C | C | C | C | C | C |
| E7 | C | C | C | C | C | C | C | C | C |
| E8 | C | C | C | CS | CS | CS | C | C | C |
| Comparative Crillet 3 | C | C | C | C | C | C | C | C | C |
| Comparative Brij S20 | St | C | C | C | C | C | C | C | C |
| Comparative Polyaldo 10-1 O KFG | C | C | C | C | C | C | C | C | C |
| Comparative Natpure SOL | C | C | C | C | C | C | C | C | C |

| | Oil | | | | | | | | |
|---|---|---|---|---|---|---|---|---|---|
| | IPM (5% NaCl) | | | Mineral Oil | | | Mineral Oil (5% NaCl) | | |
| Emulsifier | day | week | month | day | week | month | day | week | month |
| E1 | C | C | C | C | C | C | C | C | C |
| E2 | C | C | C | C | C | C | C | C | C |

TABLE TWO-continued

| | | | | | | | | | |
|---|---|---|---|---|---|---|---|---|---|
| E3 | C | C | C | C | C | C | C | C | C |
| E4 | C | C | C | C | C | C | C | C | C |
| E5 | CS | CS | CS | C | C | C | CS | CS | CS |
| E6 | C | C | C | C | C | CC | C | C | CC |
| E7 | C | C | C | C | C | C | C | C | C |
| E8 | C | CS | CS | C | C | C | C | CS | CS |
| Comparative Crillet 3 | C | C | C | C | C | C | C | C | C |
| Comparative Brij S20 | C | C | C | C | C | C | C | C | C |
| Comparative Polyaldo 10-1 O KFG | C | C | C | C | C | C | C | C | C |
| Comparative Natpure SOL | C | CC | C | C | C | C | C | CC | CC |

St is Stable
C is Creamed
CC is Coalescence and Creaming
CS is Complete split of emulsion The results show for both polyglycerol oligoesters according to the invention and comparative emulsifiers that as only a small amount of water phase thickener was used and there was no coemulsifier present then the particle size was not small enough to retard creaming. However, the results do show that polyglycerol oligoesters according to the invention have similar or equivalent stability to commercial EO-containing and commercial green emulsifiers. In some cases the polyglycerol oligoesters according to the invention would only be suitable for use in personal care applications where there are no salts present.

Example 3

Each S as defined in Table One was tested for solubilisation in a variety of oils as follows. 0.1 g of oil was added to 4.0 g of a 50% aqueous solution of novel polyglycerol oligoester and these were mixed together before the slow addition of 5.0 g water. The results are in Table Three.

Materials in Table Three and Table Four (Example 4)
Emollient esters and ethers all ex Croda
HD Arlamol HD
PS15E Arlamol PS15E
AB Crodamol AB
IPM Crodamol IPM
 Essential Oils
LG Lemongrass essential oil ex R.C. Treatt
Gin Ginger essential oil Chinese ex R.C. Treatt
SP Spearmint Oil ex Fragrance oil (Int) Ltd
Tea Teatree oil ex R. C Treatt
 Fragrances
AF Aloe fresh fragrance ex Bell Fragrances
CP Couch Potato fragrance ex Ungerer Ltd
FF Firm Fruits fragrance ex Fragrance oils (Int) Ltd
GF Glaze Fresh fragrance ex Fragrance oils (int) Ltd
PO Passion flower & Orchid fragrance ex Ungerer Ltd
Si Sinodor ex Givaudon
WC White Coffee fragrance ex Fragrance oils (Int) Ltd
 Actives
MS methyl salicylate ex S Black
TA tocopheryl acetate ex BASF
 Comparative Solubilisers
Crillet 1 EO-containing ex Croda
Crodasol AC EO-containing ex Croda

TABLE THREE

| | Oil | | | |
|---|---|---|---|---|
| Solubiliser | IPM | HD | LG | Gin |
| S1 | Clear | Clear | Haze | Slight haze |
| S2 | Clear | Clear | Slight haze | Slight haze |
| S3 | Clear | Slight haze | Clear | Clear |
| Comparative Crillet 1 | Clear | Slight haze | Clear | Clear |
| Comparative Crodasol AC | Clear | Clear | Clear | Clear |

The results are indicative of the novel polyglycerol oligoester of the invention being able to act as a solubiliser for the defined oils.

Example 4

Blends of novel polyglycerol oligoester with polyol monoesters were tested for solubilisation in a variety of oils as follows. 0.2 g of test oil was added to 2 g of blend in a 15 g vial and mixed until homogeneous before addition of 10 g deionised water. If the solution was found to be clear then solubilisation testing was repeated at a lower solubiliser to oil ratio until cloudy. Conversely if the solution was found to be cloudy then solubilisation testing was repeated at a higher solubiliser to oil ratio. The solutions were left at room temperature and checked after 24 hours to assess stability of solubilisation. The results are shown in Table Four.

Materials in Table 4
Solubiliser blends of the invention
Blend A 40% S1, 40% PME1 and 20% deionised water
Blend B 32% S1, 48% PME2 and 20% deionised water

TABLE FOUR

| | Solubiliser | | |
|---|---|---|---|
| | Blend A | Blend B | Comparative Crillet 1 |
| Oil | Lowest Solubiliser to Oil ratio for clear solution stable after 24 hrs | | |
| HD | 16 | 16 | >20 |
| PSE15 | 2.4 | 5.6 | 7 |
| AB | 7.2 | 4 | 15 |
| IPM | 9.6 | 8 | >20 |
| LG | 8 | Not tested | 10 |
| CP | 4.8 | Not tested | 5 |
| Gin | 4 | 8 | 6 |
| SP | 12 | Not tested | 10 |

TABLE FOUR-continued

| | Solubiliser | | |
|---|---|---|---|
| Oil | Blend A | Blend B | Comparative Crillet 1 |
| | Lowest Solubiliser to Oil ratio for clear solution stable after 24 hrs | | |
| Tea | 5.6 | Not tested | 5 |
| PO | 3.2 | Not tested | 3 |
| AF | 4.8 | Not tested | 5 |
| GF | 5.6 | Not tested | 5 |
| Si | 6.4 | 6.4 | 20 |
| WC | 3.2 | Not tested | 3 |
| FF | 4.8 | Not tested | 5 |
| MS | 8 | Not tested | 10 |
| TA | 12 | 8 | >20 |

It can be seen from Table Four that in the majority of cases the blends are as good as or superior to known EO-containing solubilisers.

Example 5

The counter irritancy effect of Blends A and B was tested against the irritation activity of sodium lauryl sulphate (SLS) when patch tested on human skin.

Blend A

A total of 12 human volunteers were recruited for this study and the testing was carried out on the volar forearm. All experiments were carried out in a humidity controlled lab with a temperature of 21±1° C. and relative humidity of 50±5%. The products tested were:

Water
1% SLS (sodium laurly sulphate) in water (w/w)
1% SLS+1% Blend A in water (w/w)
1% SLS+5% Blend A in water (w/w)
1% SLS+10% Blend A in water (w/w)

All sites were randomised and 50 μl of the test product was applied onto a filter paper which covered an area of approximately 1 cm$^2$. Basal TEWL and inflammation (Laser Doppler) readings were taken followed by application of the product under occlusion for 24 hours. 1 hour prior to testing, the patches were removed and TEWL and inflammation readings were taken again.

Outliers were removed using the Grubbs test and the statistics were carried out using an ANOVA.

Results and Discussion

The TEWL data of FIG. 1 shows that the actual process of occluding the skin for 24 hours results in an increase in water loss through the skin when only water is the test product. Application of 1% SLS resulted in a significant increase in water loss through the skin ($p<0.001$), as would be expected.

Addition of 1% SLS combined with 1% Blend A resulted in an increase in TEWL which was significant to the water control ($p<0.01$). However, the increase seen with 1% Blend A was lower than that of 1% SLS alone, indicating counter-irritancy properties of Blend A ($p<0.001$).

Comparing the test site of water to 1% SLS added with 5% and 10% Blend A, the increase is not significantly different to the control site. This demonstrates that barrier disruption produced by SLS can be countered by the use of 5% and 10% Blend A. The TEWL values obtained for both 5% and 10% Blend A are significantly lower than the SLS only treated site ($p<0.001$).

1% Blend A does not work as well as 5% and 10% S140 in reducing the TEWL ($p<0.05$, $p<0.01$ respectively). However, both 5% and 10% Blend A work as effectively as each other in reducing the TEWL.

Figure 2:
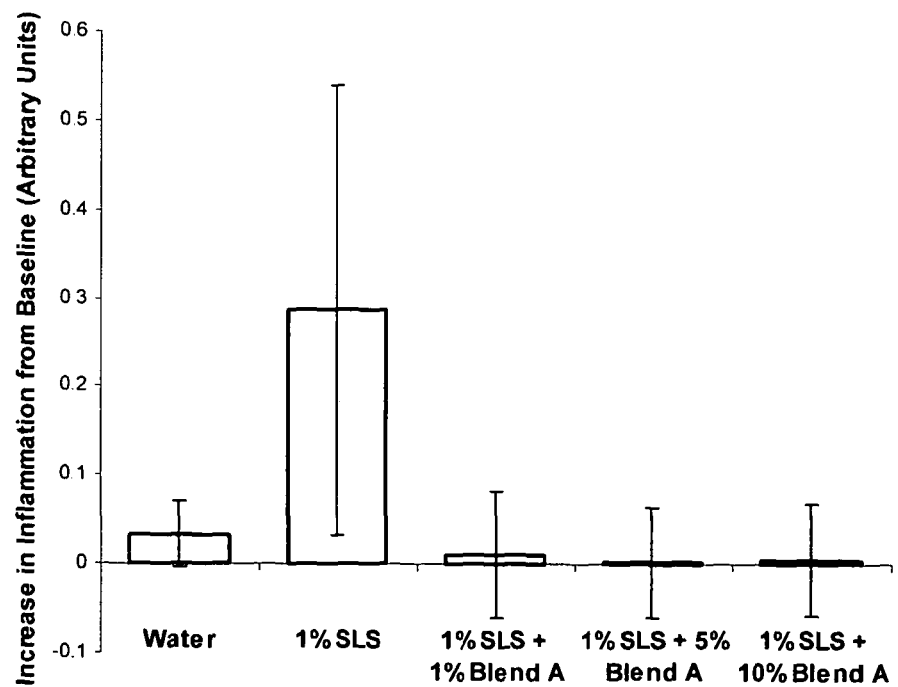
FIG. 2: Is a graph reporting Inflammation (Laser Doppler) results of Blend A with sodium lauryl sulphate (SLS).

Inflammation measurements in FIG. 2 showed that 1% SLS leads to a significant increase in inflammation compared to water ($p<0.001$). No significant increase in inflammation compared to water was seen when 1% SLS was used in addition to 1%, 5% and 10% Blend A. This proves that Blend A has counter-irritancy activity. No differences in counter-irritancy were seen when looking between 1%, 5% and 10% S140.

Blend B

Figure 3:
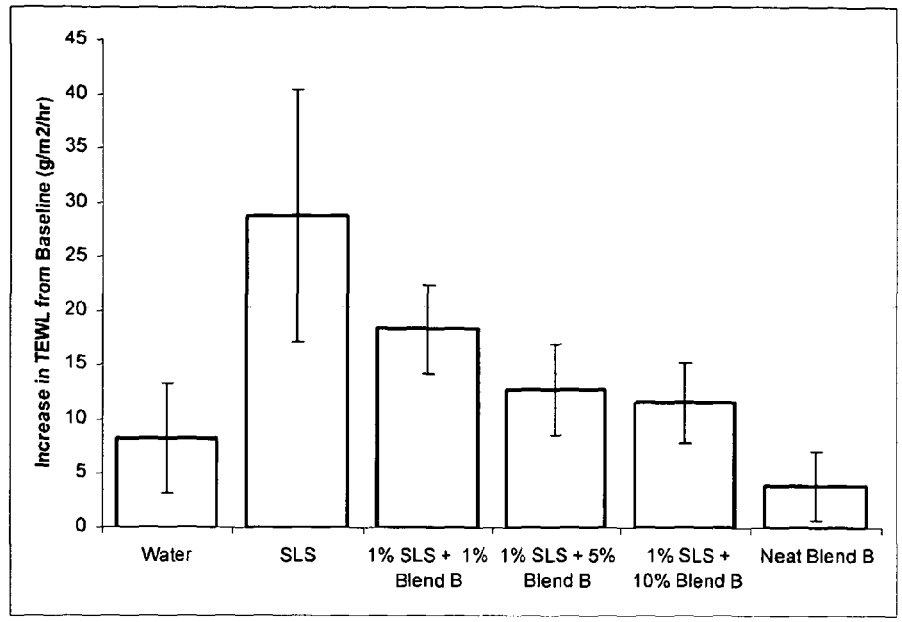
FIG. 3: Is a graph reporting Basal TEWL results of Blend B with sodium lauryl sulphate (SLS).
Figure 4:
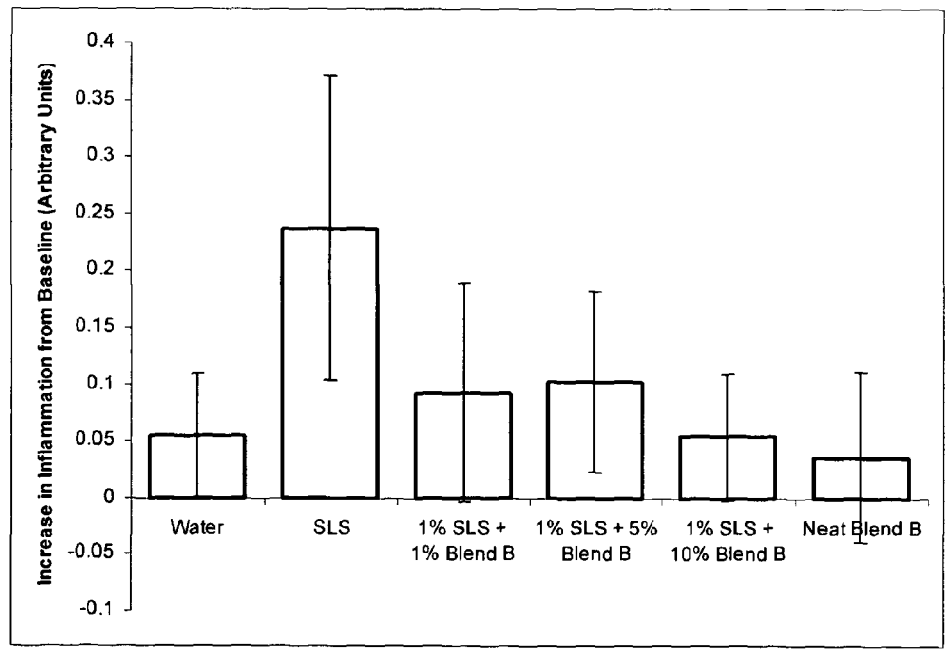
FIG. 4: Is a graph reporting Inflammation (Laser Doppler) results of Blend B with sodium lauryl sulphate (SLS).

The method carried out for Blend A was repeated for Blend B. In the method for Blend B, Blend B is directly substituted for Blend A. The TEWL and inflammation results are shown in FIGS. 3 and 4, respectively.

The TEWL data shows that the actual process of occluding the skin for 24 hours results in an increase in water loss through the skin when only water is the test product. Application of 1% SLS resulted in a significant increase in water loss through the skin ($p<0.001$), as would be expected.

Addition of 1% SLS combined with 1% Blend B resulted in an increase in TEWL which was significant to the water control ($p<0.001$). However, the increase seen with 1% Blend B was lower than that of 1% SLS alone, indicating counter-irritancy properties of Blend B ($p<0.001$).

Comparing the test site of water to 1% SLS added with 5% and 10% Blend B, the increase is not significantly different to the control site. This demonstrates that barrier disruption produced by SLS can be countered by the use of 5% and 10% Blend B. When the water control site was compared to the 'neat' Blend B applied site, no statistical significance was obtained in TEWL, demonstrating that the product itself did not have any irritancy potential.

1% Blend B does not work as well as 5% and 10% Blend B in reducing the TEWL ($p<0.05$, $p<0.01$ respectively). However, both 5% and 10% work as effectively as each other in reducing the TEWL.

Inflammation measurements showed that 1% SLS leads to a significant increase in inflammation compared to water ($p<0.001$). No significant increase in inflammation compared to water was seen when 1% SLS was used in addition to 1%, 5% and 10% Blend B. This proves that Blend B has counter-irritancy activity. No differences in counter-irritancy were seen when looking between 1%, 5%, 10% Blend B and the 'neat' product.

Conclusion

The irritancy and inflammation effects of 1% SLS can be mitigated with the addition of Blend A or Blend B. Blends A and B exhibit excellent counter-irritancy activity.

Example 6

Formulations for various home care products were produced according to the following compositions HC1, HC2 and HC3.

HC1 'Green' Anti-Static Window and Glass Cleaner Formulation

The main vessel ingredients were combined, with stirring, in the order listed in Table Five below. Each ingredient was ensured to be dispersed thoroughly. The pH was adjusted with triethanolamine to approximately pH 9.0.

The fragrance solubiliser and fragrance were mixed together in a separate pot and added to the main vessel.

Usage: Applied neat as a spray cleaner

TABLE FIVE

| Product | Functionality | % w/w |
|---|---|---|
| Main Vessel | | |
| Water (Aqua) | Solvent | 91.6 |
| Ethanol, biomass-derived | Solvent | 5 |
| *Crodasinic LS30 NT | Surfactant | 1.1 |
| *Synperonic NCA850 | Surfactant | 0.9 |
| *Crodastat 200 | Anti-Stat | 0.6 |
| Triethanolamine | pH Adjuster | to pH 9.0 |
| Side Pot | | |
| Blend A (see Example 4) | Fragrance solubiliser | 0.6 |
| Apple Fresh | Fragrance, CPL Aromas | 0.2 |

*ex Croda

The clear formulation gave a clean, streak-free finish, ideal for use with a trigger pack. The surfactant blend and mildly alkali formula aided the removal of residues from windows, glass and mirrors. Ethanol produced from biomass, for example sugar cane or corn, provides a sustainable feedstock. The formulation required no rinsing after use.

The fragrance, normally insoluble in aqueous systems was found to be effectively solubilised by the addition of Blend A.

HC2: 'Green' Bath and Shower Cleaner Formulation

The main vessel ingredients were combined, with stirring, in the order listed in Table Six below. Each ingredient was ensured to be dispersed thoroughly. The pH was adjusted with citric acid to approximately pH 6.0.

The solubiliser and fragrance were mixed together in a separate pot and added to the main vessel.

Usage: Applied Neat as a Spray Cleaner

TABLE SIX

| Product | Functionality | % w/w |
|---|---|---|
| Main Vessel | | |
| Water (Aqua) | Solvent | 93 |
| *Crodasinic LS30 NT | Surfactant | 3.2 |
| *Synperonic NCA850 | Surfactant | 1.8 |
| Sodium Citrate | Builder | 1 |
| Citric acid (50%) | pH Adjuster | To pH 6.0 |
| Side Pot | — | |
| Blend A | Fragrance solubiliser | 0.8 |
| Sicilian Lemon | Fragrance, CPL Aromas | 0.2 |

*ex Croda

The formulation was suitable for dispensing from a trigger pack. The surfactant blend aided the removal of soap scum and other residues from ceramic tiles and plastics. The mildly acidic formula helped the removal of limescale deposits and prevented the build up of residues on exposed surfaces. The formulation was rinsed away after cleaning with water.

The fragrance, normally insoluble in aqueous systems was found to be readily solubilised by the addition of Blend A.

HC3: 'Green' General Purpose Degreaser Formulation

TABLE SEVEN

| Product | Functionality | % w/w |
|---|---|---|
| Main Vessel | | |
| Water (Aqua) | | 82.2 |
| *Synperonic NCA850 | Surfactant | 0.8 |
| *Multitrope 810 | Hydrotrope | 1.6 |
| Sodium Metasilicate Pentahydrate | | 5.5 |
| Sodium Carbonate | Builder | 2 |
| Sodium Hydroxide | pH Adjuster | 1.5 |

TABLE SEVEN-continued

| Product | Functionality | % w/w |
|---|---|---|
| Side Pot | | |
| Blend A | Fragrance solubiliser | 0.4 |
| Fruity | Fragrance | 0.1 |

*ex Croda

The sodium metasilicate pentahydrate was added to the water followed by the sodium carbonate and sodium hydroxide. These were mixed at 20° C. for 10 minutes until a clear solution was formed. The Multitrope 810 was then added, followed by the Synperonic NCA850, and the composition was mixed for 10 minutes at 20° C. until a clear colour solution was produced.

In a side pot, the fragrance was added into Blend A, and the components were mixed until a homogenous solution was produced. The side pot solution was added to main vessel and mixed for 10 minutes at 20° C. until the solution was clear.

Usage: 2-5% as a spray or soak cleaner.

This formulation was designed for use in environments where soiling from oily or greasy processing necessitates a fast and effective cleaner. Synperonic NCA850 is a green detergent which cuts through greasy soils, whilst Multitrope 810 provides wetting and stability to the formulation.

The fragrance, normally insoluble in aqueous systems was found to be readily solubilised by the addition of Blend A.

Example 7

The amount of surfactant required to solubilise 1% of a range of lipophiles was tested for Blend A and compared against polysorbate 20 (Tween 20 ex Croda) and PEG-40 hydrogenated castor oil (Croduret 40 ex Croda). The results are shown below in Table Eight.

TABLE EIGHT

| | % Surfactant required to solubilise 1% of lipophile | | | |
|---|---|---|---|---|
| | Blend A | | Tween 20 (Polysorbate 20) | Croduret 40 (PEG-40 Hydrogenated Castor Oil) |
| Lipophile | 80% active | 100% active | 100% active | 100% active |
| Fragrances - CPL Aromas | | | | |
| Fruity | 3 | 2.4 | 5 | 6 |
| Rose Fresh | 20 | 16 | 8 | 8 |
| Apple Fresh | >20 | — | 10 | 8 |
| Orange and Mandarin | >20 | — | 8 | 8 |
| Sicilian Lemon | 15 | 12 | 6 | 12 |
| Lavender | 20 | 16 | 7 | 6 |
| Lemon Peel | 20 | 16 | 9 | 10 |
| Mandarin & Corainder | 10 | 8 | 12 | 10 |
| Peach Leaf | 15 | 12 | 7 | 10 |
| Pear Blossom & Kiwi | 12 | 9.6 | 7 | 10 |
| Tomato Leaf | >20 | — | 7 | 8 |
| *Aloe* & Lilac Fabric | 20 | 16 | 7 | 7 |
| Pure Force Fabric | 12 | 9.6 | 20 | 12 |
| Lilac & Cotton Flower Fabric | 15 | 12 | 12 | 12 |
| Fresh Air Fabric | 15 | 12 | 8 | 9 |
| White Tuberose Fabric | 15 | 12 | 5 | 4 |
| Grapefruit & Green Tea | 15 | 12 | 7 | 7 |
| Mint | 20 | 16 | 8 | 6 |

TABLE EIGHT-continued

| | % Surfactant required to solubilise 1% of lipophile | | | |
|---|---|---|---|---|
| | Blend A | | Tween 20 (Polysorbate 20) 100% active | Croduret 40 (PEG-40 Hydrogenated Castor Oil) 100% active |
| Lipophile | 80% active | 100% active | | |
| Essential Oils | | | | |
| Bergamot Oil | 4 | 3.2 | 7 | 12 |
| Citronellol | 8 | 6.4 | 7 | 12 |
| Clove Stem Oil | 12 | 9.6 | 10 | 15 |
| Lavender Oil | 10 | 8 | 10 | 10 |
| Lemon Oil | 10 | 8 | 10 | 12 |
| Limonene | 5 | 4 | 8 | 15 |
| Organic *Eucalyptus Radiata* Oil | 8 | 6.4 | 4 | 5 |
| Organic Roman Chamomile Oil | 3 | 2.4 | 8 | 5 |
| Tangerine Oil Brazil | 4 | 3.2 | 9 | 5 |
| Frequency solubiliser was most efficient | 10 | | 11 | 6 |

Example 8

Experiments have been conducted on that the addition of emulsifying waxes to a simple formulation consisting of an oil phase of isopropyl myristate and caprate/caprylate triglycerides at 7.5% each, 5% emulsifier wax blend and 80% deionised water. Comparisons have been made between systems using the novel polyglyceryl oligoester as the high HLB component of the emulsifying wax and a standard non-green, ethoxylated high HLB emulsifier, PEG-100 stearate.

The figures in Table Nine below relate to the combinations of oligoester and interfacially wax tested experimentally. All of these combinations used a ratio of 2:1:1, as the emulsifier wax blend portion of the formulation described in the paragraph above. The viscosity of this formulation was deemed successful if it was higher than that of the highest benchmark (PEG-100 stearate) result of 5100 mPa.s. Equally emulsion stability was assessed by the particle size of the emulsion a d(0.5) particle size of the same or less than that of the benchmark system 96 μm. The emulsifying wax systems tested have been identified in the table below. All of these systems are equivalent to, or an improvement on, the benchmark system without the requirement of alkoxylates, and in the presence of 10% NaCl in many cases, which is very difficult to achieve without the use of alkoxylate technology.

TABLE NINE

| Blend # | Novel Oligimer | Wax 1 | Wax 2 | NaCl level | Viscosity (mPa·s) | Particle Size (μm d (0.5)) |
|---|---|---|---|---|---|---|
| 1 | PEG-100 Stearate | Stearyl alcohol | Cetostearyl alcohol | 0% | 5100 | 98 |
| 2 | PEG-100 Stearate | Stearyl alcohol | Cetostearyl alcohol | 10% | 1750 | 96 |
| 3 | PEG-100 Stearate | Glyceryl monostearate (90% Mono) | Stearyl alcohol | 0% | 2800 | 184 |
| 4 | PEG-100 Stearate | Glyceryl monostearate (90% Mono) | Stearyl alcohol | 10% | 3100 | 255 |
| 5 | (PG4)-C4-(PG4)-PALM (2:1:0.75) | Glyceryl monostearate (90% Mono) | Cetostearyl alcohol | 0% | 11000 | 66 |
| 6 | (PG6)-C4-(PG6)-PALM (2:1:0.75) | Stearyl alcohol | Cetostearyl alcohol | 0% | 6800 | 169 |
| 7 | (PG6)-C4-(PG6)-PALM (2:1:0.75) | Stearyl alcohol | Cetostearyl alcohol | 10% | 9950 | 52 |
| 8 | (PG6)-C4-(PG6)-PALM (2:1:0.75) | Glyceryl monostearate (40% Mono) | Stearyl alcohol | 0% | 10900 | 130 |
| 9 | (PG6)-C4-(PG6)-PALM (2:1:0.75) | Glyceryl monostearate (40% Mono) | Stearyl alcohol | 10% | 13100 | 120 |
| 10 | (PG6)-C4-(PG6)-PALM (2:1:0.75) | Glyceryl monostearate (40% Mono) | Cetostearyl alcohol | 0% | 14300 | 72 |
| 11 | (PG6)-C4-(PG6)-PALM (2:1:0.75) | Glyceryl monostearate (40% Mono) | Cetostearyl alcohol | 10% | 19150 | 49 |
| 12 | (PG6)-C4-(PG6)-PALM (2:1:0.75) | Glyceryl monostearate (90% Mono) | Stearyl alcohol | 0% | 6700 | 29 |
| 13 | (PG6)-C4-(PG6)-PALM (2:1:0.75) | Glyceryl monostearate (90% Mono) | Stearyl alcohol | 10% | 6350 | 26 |
| 14 | (PG10)-C4-(PG10)-PALM (2:1:0.75) | Stearyl alcohol | n/a | 0% | 6700 | 120 |
| 15 | (PG10)-C4-(PG10)-PALM (2:1:0.75) | Cetostearyl alcohol | n/a | 0% | 11250 | 110 |
| 16 | (PG10)-C4-(PG10)-PALM (2:1:0.75) | Cetostearyl alcohol | n/a | 10% | 12150 | 59 |
| 17 | (PG10)-C4-(PG10)-PALM (2:1:0.75) | Glyceryl monostearate (40% Mono) | Stearyl alcohol | 0% | 11800 | 184 |
| 18 | (PG10)-C4-(PG10)-PALM (2:1:0.75) | Glyceryl monostearate (40% Mono) | Cetostearyl alcohol | 0% | 12350 | 118 |
| 19 | (PG10)-C4-(PG10)-PALM (2:1:0.75) | Glyceryl monostearate (40% Mono) | Cetostearyl alcohol | 10% | 11800 | 113 |
| 20 | (PG10)-C4-(PG10)-PALM (2:1:0.75) | Glyceryl monostearate (90% Mono) | Stearyl alcohol | 0% | 9150 | 122 |
| 21 | (PG10)-C4-(PG10)-PALM (2:1:0.75) | Glyceryl monostearate (90% Mono) | Stearyl alcohol | 10% | 8450 | 100 |
| 22 | (PG10)-C4-(PG10)-STEARATE (2:1:0.75) | Cetostearyl alcohol | n/a | 0% | 8700 | 83 |
| 23 | (PG10)-C4-(PG10)-STEARATE (2:1:0.75) | Glyceryl monostearate (40% Mono) | Stearyl alcohol | 0% | 5050 | 201 |
| 24 | (PG10)-C4-(PG10)-STEARATE (2:1:0.75) | Glyceryl monostearate (40% Mono) | Cetostearyl alcohol | 0% | 8300 | 112 |
| 25 | (PG10)-C4-(PG10)-STEARATE (6:5:1) | Glyceryl monostearate (40% Mono) | Cetostearyl alcohol | 0% | 4150 | 217 |
| 26 | (PG10)-C4-(PG10)-STEARATE (6:5:1) | Glyceryl monostearate (40% Mono) | Cetostearyl alcohol | 10% | 5700 | 142 |
| 27 | (PG10)-C4-(PG10)-STEARATE (6:5:1) | Glyceryl monostearate (90% Mono) | Cetostearyl alcohol | 0% | 4600 | 215 |
| 28 | (PG10)-C4-(PG10)-STEARATE (6:5:1) | Glyceryl monostearate (90% Mono) | Cetostearyl alcohol | 10% | 5100 | 222 |
| 29 | (PG10)-C4-(PG10)-STEARATE (6:5:1) | Glyceryl monostearate (90% Mono) | Stearyl alcohol | 0% | 7100 | 158 |
| 30 | (PG10)-C4-(PG10)-STEARATE (6:5:1) | Glyceryl monostearate (90% Mono) | Stearyl alcohol | 10% | 6750 | 60 |
| 31 | (PG6)-C4-(PG6)-PALM (2:1:0.9) | Glyceryl monostearate (40% Mono) | Cetostearyl alcohol | 0% | 11300 | 73 |
| 32 | (PG6)-C4-(PG6)-PALM (2:1:0.9) | Glyceryl monostearate (40% Mono) | Cetostearyl alcohol | 10% | 21100 | 43 |
| 33 | (PG6)-C4-(PG6)-PALM (2:1:0.9) | Glyceryl monostearate (90% Mono) | Stearyl alcohol | 0% | 7500 | 73 |
| 34 | (PG6)-C4-(PG6)-PALM (2:1:0.9) | Glyceryl monostearate (90% Mono) | Stearyl alcohol | 10% | 16600 | 51 |
| 35 | (PG6)-C4-(PG6)-PALM (2:1:2) | Glyceryl monostearate (40% Mono) | Cetostearyl alcohol | 0% | 6700 | 80 |
| 36 | (PG6)-C4-(PG6)-PALM (2:1:2) | Glyceryl monostearate (40% Mono) | Cetostearyl alcohol | 10% | 25250 | 46 |
| 37 | (PG6)-C4-(PG6)-PALM (2:1:2) | Glyceryl monostearate (90% Mono) | Stearyl alcohol | 0% | 7050 | 33 |
| 38 | (PG6)-C4-(PG6)-PALM (2:1:2) | Glyceryl monostearate (90% Mono) | Stearyl alcohol | 10% | 23400 | 32 |

The invention claimed is:

1. A polyglycerol oligoester prepared by reacting reactants consisting essentially of:
   i) a polyglycerol having from 3 to 20 glycerol units;
   ii) a dicarboxylic acid or cyclic anhydride of such dicarboxylic acid having from 4 to 22 carbon atoms; and
   iii) a linear, saturated monocarboxylic acid having from 4 to 24 carbon atoms; in a molar ratio from 1.5:1.0:0.5 to 2.5:1:1.2;
   wherein the polyglycerol oligoester has an HLB in the range of between 13 to 16.

2. A polyglycerol oligoester of claim 1, wherein the polyglycerol has 4 to 10 glycerol units.

3. A polyglycerol oligoester of claim 1, wherein the dicarboxylic acid is represented by the formula HOOC—R—COOH where R is a group —$(CH_2)_n$- where n is from 2 to 20.

4. A polyglycerol oligoester of claim 1, wherein the monocarboxylic acid is represented by the formula $R^1COOH$ and $R^1$ is a $C_5$ to $C_{21}$ alkyl, alkenyl or alkadienyl group.

5. A polyglycerol oligoester of claim 1, further comprising a second polyglycerol oligoester wherein the ratio of the first polyglycerol oligoester to the second polyglycerol oligoester ranges from 9:1 to 1:9.

6. A method of making the polyglycerol oligoester of claim 1, comprising:
   reacting polyglycerol having from 3 to 20 glycerol units with a dicarboxylic acid or cyclic anhydride of such dicarboxylic acid having from 4 to 22 carbon atoms and a monocarboxylic acid having from 4 to 24 carbon atoms in a molar ratio from 1.5:1.0:0.5 to 2.5:1:1.2 together in a single stage under esterification conditions;
   wherein the polyglycerol oligoester has an HLB in the range of between 13 to 16.

7. A method of making the polyglycerol oligoester of claim 1, comprising:
   a) reacting polyglycerol having from 3 to 20 glycerol units with a dicarboxylic acid or cyclic anhydride of such dicarboxylic acid having from 4 to 22 carbon atoms in a molar ratio from 1.5:1.0 to 2.5:1 under esterification conditions to form a precursor polyglycerol oligoester;
   b) monitoring the esterification until the reaction mixture has reached an acid value of 0 to 5 mgKOH/g; then
   c) adding 0.5 to 1.2 moles relative to dicarboxylic acid reactant of a monocarboxylic acid having from 4 to 24 carbon atoms;
   wherein the polyglycerol oligoester has an HLB in the range of between 13 to 16.

8. A method of emulsifying, solubilizing, and/or thickening a personal care and/or home care formulation, comprising using the polyglycerol oligoester of claim 1 as an emulsifier, solubiliser and/or thickener.

9. A personal care and/or home care formulation comprising at least an emulsifier, solubiliser and/or thickener, wherein the emulsifier, solubiliser and/or thickener comprises the polyglycerol oligoester of claim 1.

10. A blend of
    a) a polyglycerol oligoester of claim 1; and
    b) a polyol monoester,
    wherein the ratio of a): b) ranges from 5.0:1.0 to 1.0:5.

11. The blend of claim 10, wherein the ratio of a):b) ranges from 3.0: 1.0 to 1.0:3.0.

12. The blend of claim 10, wherein the polyol is chosen from neopentyl polyols and polyglycerols.

13. A method of solubilizing a personal care, health care and/or home care formulation, comprising using the polyglycerol oligoester of claim 10 as a solubilizer.

* * * * *